(12) United States Patent
Siochi

(10) Patent No.: US 6,240,161 B1
(45) Date of Patent: *May 29, 2001

(54) MULTI-LEAF COLLIMATOR CONSTRAINED OPTIMIZATION OF INTENSITY MODULATED TREATMENTS

(75) Inventor: Ramon Alfredo Siochi, Fairfield, CA (US)

(73) Assignee: Siemens Medical Systems, Inc., Iselin, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/936,299

(22) Filed: Sep. 25, 1997

(51) Int. Cl.[7] .................................................. G21K 5/08
(52) U.S. Cl. ............................................................ 378/65
(58) Field of Search ............................................... 378/65

(56) References Cited

U.S. PATENT DOCUMENTS

| | | | |
|---|---|---|---|
| 3,987,281 | 10/1976 | Hodes | 235/151.3 |
| 5,148,032 | 9/1992 | Hernandez | 250/492.1 |
| 5,339,812 | 8/1994 | Hardy et al. | 128/653.1 |
| 5,418,827 | 5/1995 | Deasy et al. | 378/65 |
| 5,438,991 | 8/1995 | Yu et al. | 128/653.1 |
| 5,563,925 | 10/1996 | Hernandez | 378/150 |
| 5,602,892 | 2/1997 | Llacer | 378/65 |
| 5,625,663 | 4/1997 | Swerdloff . | |
| 5,647,663 | 7/1997 | Holmes . | |
| 5,663,999 | 9/1997 | Siochi | 378/65 |
| 5,751,781 | * 5/1998 | Brown et al. | 378/65 |
| 5,818,902 | * 10/1998 | Yu | 378/65 |
| 5,936,089 | * 8/1999 | Carpino et al. . | |

OTHER PUBLICATIONS

George Starkschall, "A Constrained Least–Squares Optimization Method for External Beam Radiation Therapy Treatment Planning," Medical Physics, vol. 11, No. 5, Sep./Oct. 1984, pp. 659–665.

William A. Sandham, et al., "Conformal Therapy Using Maximum Entropy Optimization," International Journal of Imaging Systems & Technology, vol. 6, (1995), pp. 80–90.

Anders Brahme, "Optimization of Stationary and Moving Beam Radiation Therapy Techniques," Radiotherapy and Oncology, Journal of the European Society for Therapeutic Radiology & Oncology, vol. 12, No. 2, (1988), pp. 129–140.

S. Webb, "Optimisation of Conformal Radiotherapy Dose Distributions by Simulated Annealing," Physics in Medicine and Biology, vol. 34, No. 10, (1989), pp. 1349–1370.

Thomas Bortfeld & Wolfgang Schlegel, "Optimization of Beam Orientations in Radiation Therapy: Some Theoretical Considerations," Physics in Medicine and Biology, vol. 38, No. 2, (1993), pp. 291–304.

Steve Webb, "Optimizing Radiation Therapy Inverse Treatment Planning Using the Simulated Annealing Technique," International Journal of Imaging Systems & Technology, vol. 6, No. 1, (1995), pp. 71–79.

S. Webb, "Optimization by Simulated Annealing of Three–Dimensional Conformal Treatment Planning for Radiation Fields Defined by a Multileaf Collimator," Physics in Medicine & Biology, vol. 36, No. 9, (1991), pp. 1201–1226.

(List continued on next page.)

*Primary Examiner*—Craig E. Church

(57) ABSTRACT

A system and method for radiation therapy delivery. The present invention provides for optimizing radiation delivery by accounting for the physical attributes of a beam shielding device (401) when determining an optimal radiation treatment. These include, for example, constraining the optimization engine with realizable positioning of plates and/or collimator leaves. Thus, an optimal set of fields and intensity levels for those fields are chosen.

17 Claims, 5 Drawing Sheets

OTHER PUBLICATIONS

Journal of Organic Chemistry, Bd. 43, Nr. 15, 1978 Seiten 2949–2952, XP002134569, C. B. Ziegler, Jr. et al, "Palladium–Catalyzed Vinylic Substitution Reactions of N–Vinyl Amides"

Journal of Organic Chemistry, Bd. 57, Nr. 13, 1992 Seiten 3558–3563, XP002134568, Walter Cabri et al "Palladium--catalyzed Arylation of Unsymmetrical Olefins. Bidentate Phosphine Ligand Controlled Regioselectivity."

* cited by examiner

MULTI-LEAF COLLIMATOR CONSTRAINED OPTIMIZATION OF INTENSITY MODULATED TREATMENTS

BACKGROUND OF THE INVENTION

The present invention relates to a radiation emitting device, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist. The prescription is a definition of, for example, a particular volume and the level of radiation permitted to be delivered to that volume. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and delivered intensity levels to optimize the dose volume histograms, which define a cumulative level of radiation which is to be delivered to a specified volume. Typical optimization engines optimize the dose volume histograms by considering the oncologist's prescription, or three-dimensional specification of dosage to be delivered. In such optimization engines, the three-dimensional volume is broken into cells, each cell defining a particular level of radiation to be administered. The outputs of the optimization engines are intensity maps, which are determined by varying the intensity at each "cell" in the map. The intensity maps specify a number of fields defining desired (optimized) intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible. However, such optimization engines do not account for the beam shielding device itself; the output intensity map is simply a level of dosage to be applied at a particular cell.

More particularly, once the optimization routines define a plurality of intensity levels at each cell, the beam shielding device settings must be chosen according to the output number of fields. Often, however, the output of such routines define a number of fields that would require a prohibitive amount of time to deliver, or which is physically impossible for the beam shielding device to achieve. Thus, to provide a realizable dosage, fewer intensity levels must be provided, or fewer fields, and the dose volume histograms are thereby degraded. While methods are known for efficiently arranging leaf positions to deliver dosages according to the intensity maps (e.g., U.S. Pat. No. 5,663,999, assigned to Siemens Medical Systems, Inc.), such systems may still cause a degradation of the dose volume histogram.

Accordingly, there is a need for a system and method for determining radiation delivery which accounts for the system's physical constraints.

SUMMARY OF THE INVENTION

These problems in the prior art are overcome in large part by a system and method for radiation therapy delivery according to the present invention. More particularly, rather than determining a number of beam shielding device settings after one or more optimized intensity maps have been determined, the present invention accounts for the physical attributes of a beam shielding device when determining an optimal radiation treatment. These include, for example, realizable positioning of plates and/or collimator leaves. Thus, an optimal set of fields and intensity levels for those fields are chosen, and a sequence of beam shielding device settings which are optimized to the actual device are output.

According to one embodiment of the invention, a user selects a number of beams and collimator and/or plate fields. The user also selects a dose volume histogram, or prescription, for each volume of interest. The routine then selects an initial set of leaf positions and a field intensity for each field. The initial selection is determined by shaping the leaf field to the tumor and choosing higher intensities where there is a higher tumor volume. The dose volume histograms are calculated and a figure of merit is determined which measures how closely the calculated dose volume histograms match the specified dose volume constraints for the region of interest. The leaf positions and the field intensities for each field are then varied according to an optimization algorithm such as simulated annealing and the figure of merit is evaluated again. Several iterations occur until either the figure of merit no longer improves or reaches a predetermined threshold. The fields for each beam are then arranged in an autosequence that will reduce the amount of leaf travel.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
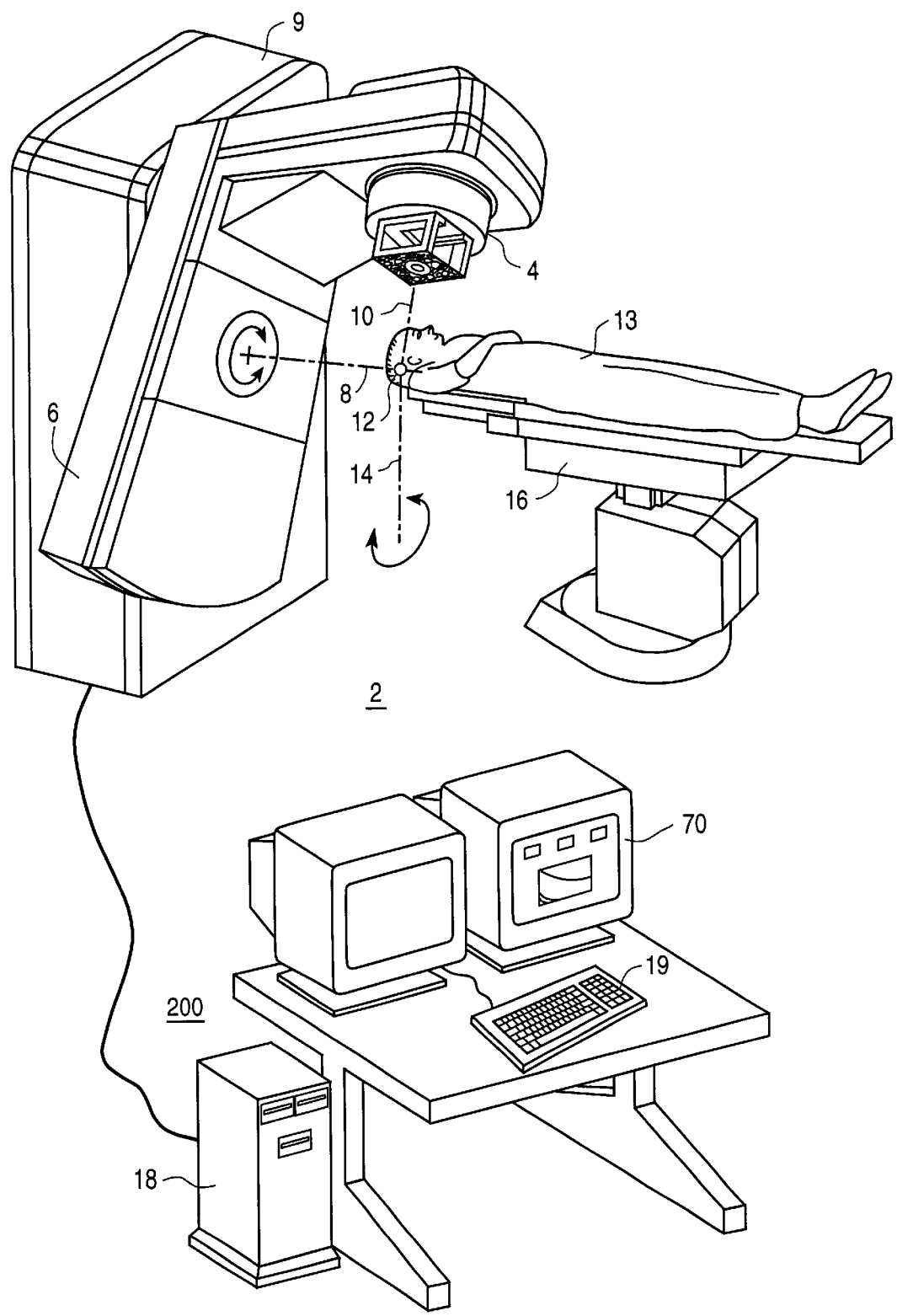
FIG. 1 is a diagram of a radiation treatment device and treatment console according to an embodiment of the present invention.

Referring to the drawings and especially to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such a data storage device. Various data can be displayed before and during the treatment on the screen of the monitor 70.

Figure 2:
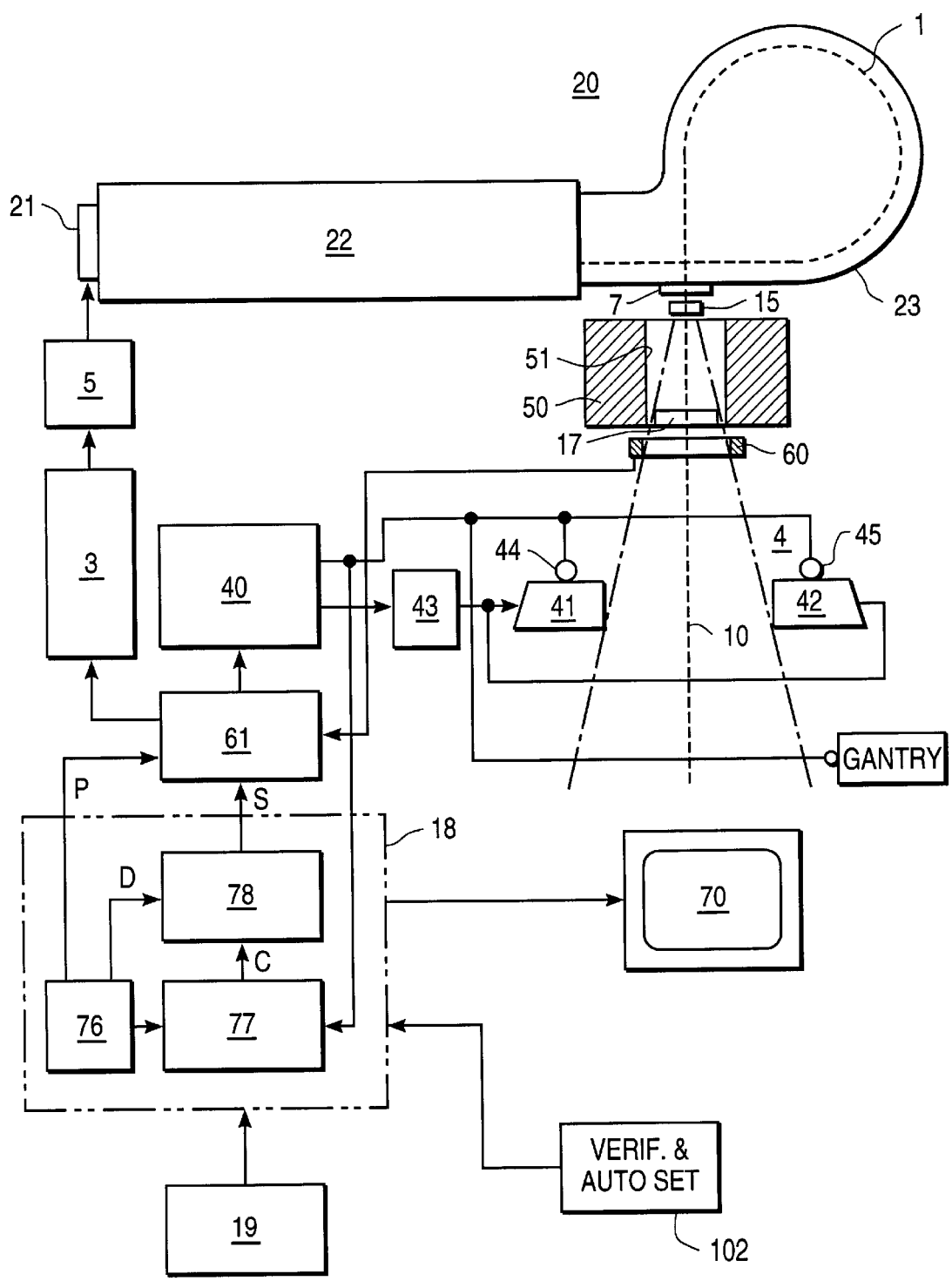
FIG. 2 is a more detailed block diagram illustrating portions of the present invention.

Turning now to FIG. 2, a block diagram of the radiation treatment device 2 and portions of the treatment unit 200 are illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source (not shown) is provided, which supplies radio frequency signals for the generation of an electromagnetic field supplied to the wave guide 22. The electrons injected by the injector 5 and emitted by the electron gun 21 are accelerated by this electromagnetic field in the wave guide 22 and exit at the end opposite to electron gun 21 in electron beam 1. The electron beam 1 then enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 includes a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 2 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions. As discussed above, the plate arrangement 401 may alternatively include a multi-leaf collimator having many radiation blocking leaves.

Figure 3:
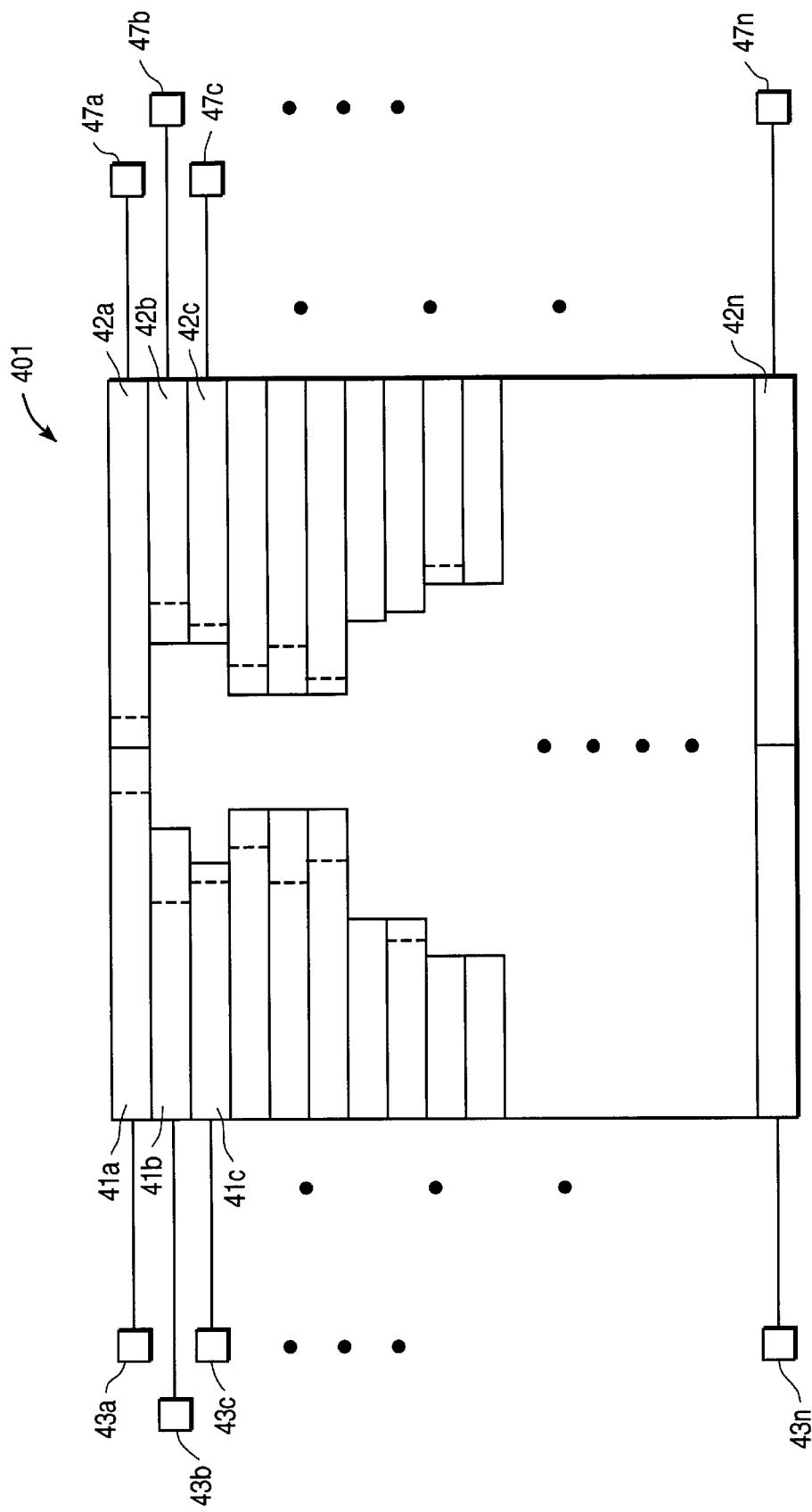
FIG. 3 is a diagram of a multi-leaf collimator according to an embodiment of the invention.

The leaves of such a multi-leaf collimator are illustrated in greater detail in FIG. 3. Opposing leaf, or rod pairs 41a–41n, 42a–42n, each include a motor or drive unit 43a–43n, and 47a–7n, respectively. The drive units drive the rods, or leaves, in and out of the treatment field, thus creating the desired field shape. The rods, or leaves, are relatively narrow, and cast a shadow of about 0.5 to 1.0 cm at isocenter.

Turning back to FIG. 2, the motor controller 40 is coupled to a dose unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. In such a radiation device, the dose absorbed by the object 13 is dependent upon movement of the collimator leaves.

The central processing unit 18 is programmed by the therapist according to the instructions of the oncologist and performs optimization according to the present invention so that the radiation treatment device carries out the prescribed radiation treatment. The delivery of the radiation treatment is input through a keyboard 19. The central processing unit 18 is further coupled to a dose control unit 61 that generates the desired values of radiation for controlling trigger system 3. Trigger system 3 then adapts the pulse radiation frequency and other parameters in a corresponding, conventional manner. Central processing unit 18 further includes a control unit 76 which controls execution of the program and the opening and closing of the collimator plates 41, 42 according to the present invention to deliver radiation according to a desired intensity profile.

Figure 4A:
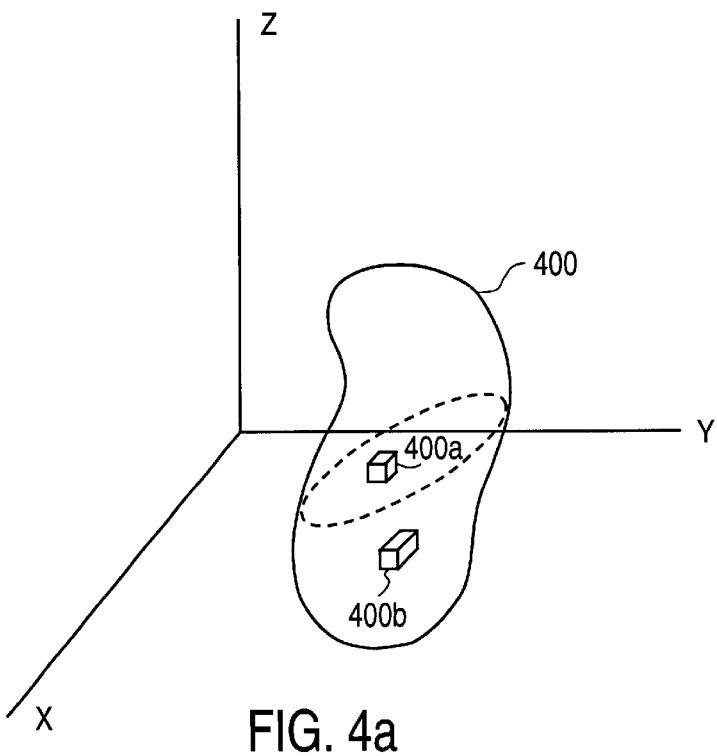
FIG. 4a and FIG. 4b are diagrams of exemplary intensity profiles.

FIG. 4 is a three dimensional illustration of a volume to be treated with radiation. The amount of radiation to be delivered to the volume 400 is not uniform throughout the volume, however. Typically, the amount of radiation to be delivered is highest in the center and decreases outwardly, though not necessarily uniformly. Thus, for example, voxels 400*a* and 400*b* could receive different levels of radiation.

Figure 4B:
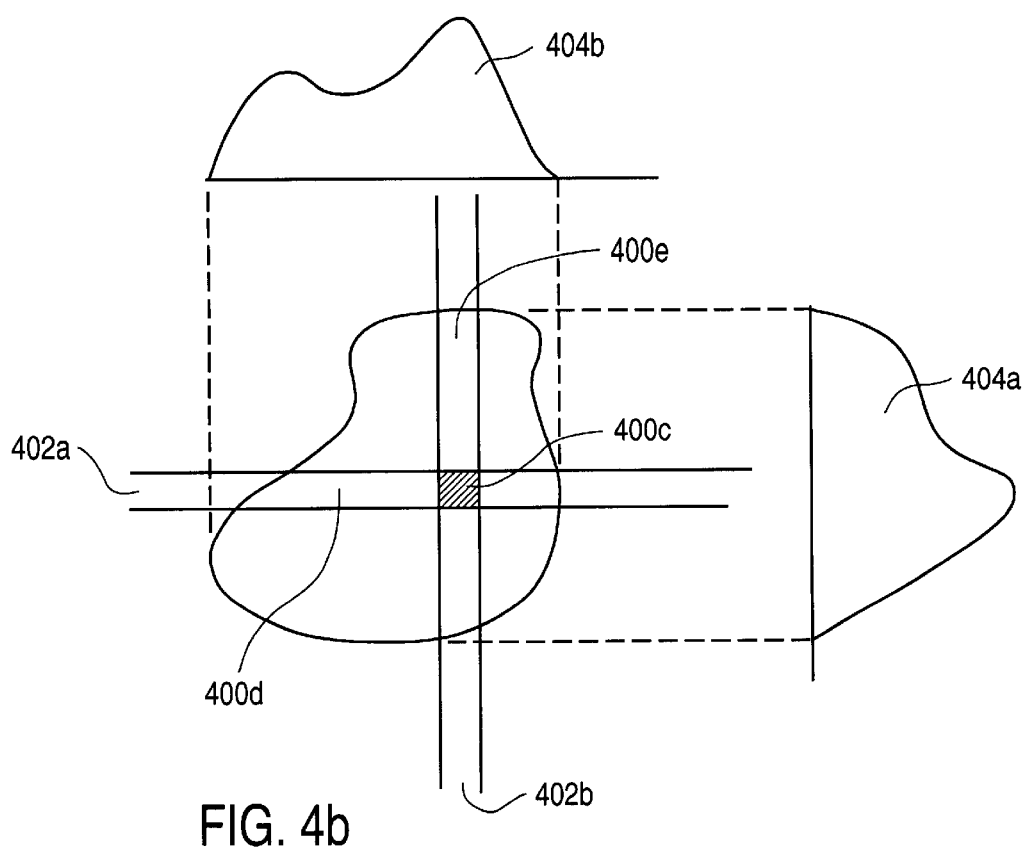

In order to deliver radiation to a specified volume a plurality of beam settings is typically applied. For example, FIG. 4*b* illustrates a two-dimensional slice of the volume 400 of FIG. 4*a*. A pair of intersecting radiation beams 402*a*, 402*b* deliver a radiation dose to the volume. The beams 402*a* and 402*b* intersect in the cross hatch region 400*c*, though radiation is delivered along the paths of each of the beams to the volumes 400*d* and 400*e*. As can be appreciated, the goal of radiation therapy is to deliver as close a dosage as possible to the prescribed dosage requirements at each of the voxels 400*a*, 400*b* etc. The goal of treatment optimization is to determine the best way to achieve this treatment fitting. As shown in FIG. 4*b* the radiation beams 402*a* and 402*b* coming from intensity profiles 404 and 404*b*, respectively, at particular gantry angles (an intensity profile is the radiation field over a line of radiation which corresponds to the slice) affect dose volume histograms 404*a*. Each gantry angle, however, may define a plurality of radiation fields which are to be delivered. Each field is defined as a number of monitor units of dosage to be delivered to a given volume at a particular gantry angle. The leaves of the multi-leaf collimator delimit the radiation beam at particular angles and thus define the fields for the particular gantry angle.

Typical optimization engines determine a non-uniform distribution of intensity levels over the treatment area which is required to deliver a dosage which is as close to the dose volume histograms as possible. However, in order to constrain the delivery time to a reasonable period, the therapist may implicitly choose a predetermined number of fields as a maximum number of fields which are to be delivered, including a number of gantry angle settings, by choosing fewer intensity levels. Because this maximum number of MLC fields is determined after optimization, the actual treatment delivery is typically suboptimal. According to the present invention, however, the number of static fields to be delivered is input to the controller 18 as an optimization variable. Similarly, the collimator leaf settings are defined at predetermined positions and also used as optimization variables. Thus, the constraints of the multi-leaf collimator and delivery time are explicitly brought into the optimization routine as will be discussed in greater detail below.

Figure 5:
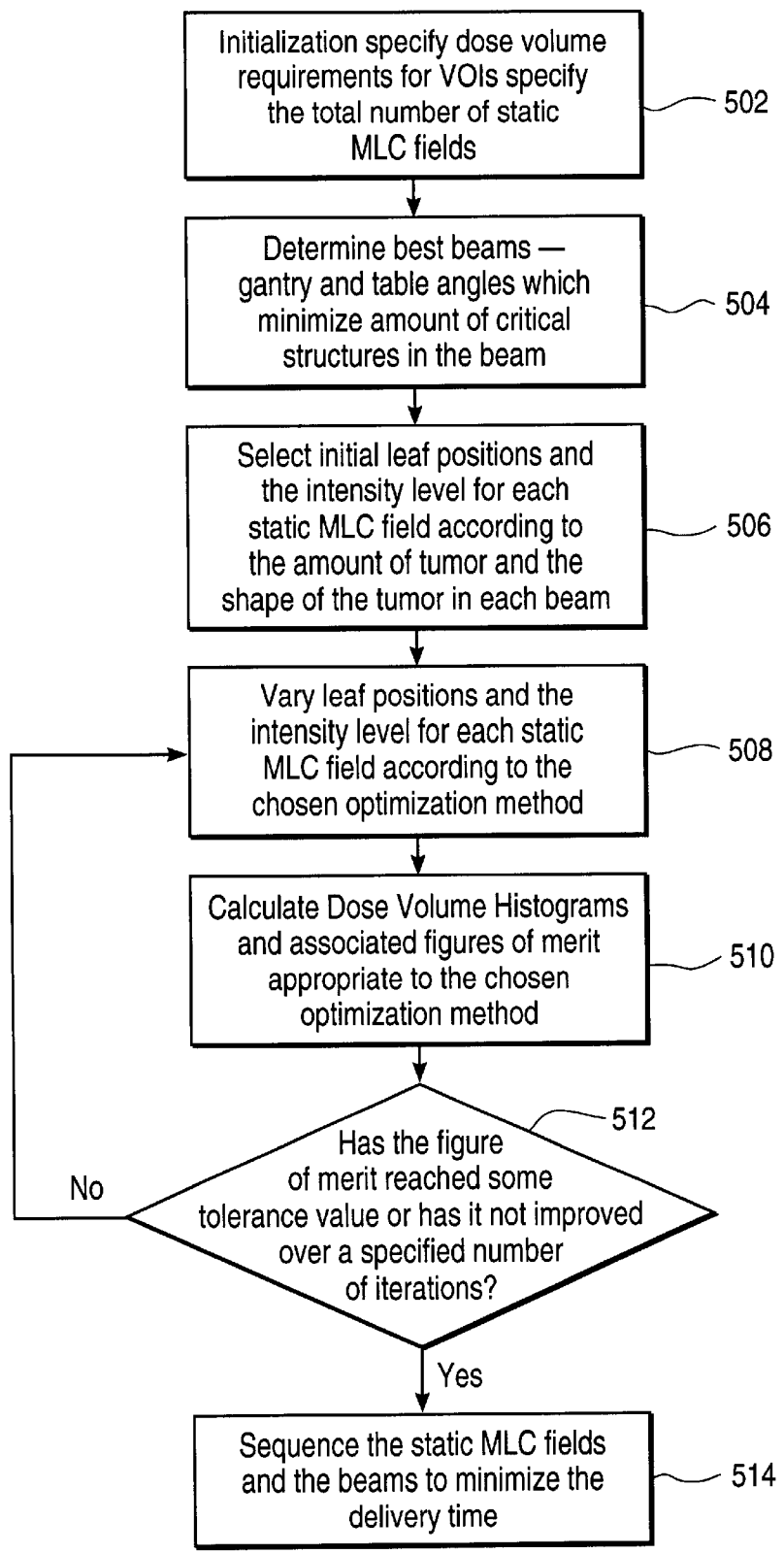
FIG. 5 is flowchart illustrating a method according to an embodiment of the invention.

A flowchart illustrating this process is shown in FIG. 5. In a step 502, an initialization occurs. The initialization specifies dose volume requirements (i.e., a prescription dose volume histogram is identified) for a particular volume of interest, for example, volume 400 of FIG. 4*a*. In addition, a total number of static multi-leaf collimator fields for delimiting the radiation beams is identified. As discussed above, the total number of static multi-leaf collimator fields relates to a predetermined number of gantry and leaf settings. In a step 504, a processor 18 determines the best beams, i.e., the gantry and table angles which minimize the amount of critical structures (i.e., physiologically important, e.g., heart, lungs, spinal cord, etc.) within the path of the beam. In a step 506, a set of initial leaf positions and radiation field intensity levels for each static MLC fields are chosen according to the amount of tumor and the shape of the tumor within each beam. Next, in a step 508, leaf positions and intensity levels for the static multi-leaf collimator fields are varied by the processor 18 according to the chosen optimization method. Exemplary optimization methods include simulated annealing, Nelder-Mead downhill simplex method, conjugate gradient methods, and mixed integer programming, which are known in the art. It is noted that other optimization algorithms may be employed; this list is exemplary only. In a step 510, dose volume histograms and associated figures of merit appropriate to the chosen optimization method are calculated. The calculated dose volume histogram associated with the chosen optimization method is compared with the prescription dose volume requirement initialized in step 502. If the figure of merit has reached a predetermined tolerance value (step 512) (i.e., if the calculated and prescription dose volume histograms are within a predetermined value of one another) then in a step 514, the static multi-leaf collimator fields are sequenced to minimize the delivery time in a step 514. If in step 512 the figure of merit had not improved over a specified number of iterations then step 514 will also occur. Thus, rather than obtaining beam shielding device settings by matching physical beam-shielding device settings to an optimized intensity map or maps, a system according to the present invention accommodates the physical beam-shielding device settings during the optimization procedure. In this fashion, a more optimal dose volume histogram may be delivered.

The invention described in the above detailed description is not intended to be limited to the specific form set forth herein, but is intended to cover such alternatives, modifications, and equivalents as can reasonably be included within the spirit and scope of the appended claims.

What is claimed is:

1. A method for delivering radiation from a radiation source to a body, comprising:

specifying a prescription dose volume histogram defining dosages to be delivered to said body;

defining a predetermined number of fields on the body for delivering said dosages;

selecting an initial setting of leaves of a multi-leaf collimator for delimiting each field;

selecting a radiation field intensity for each field;

determining a calculated dose volume histogram corresponding to said openings;

comparing said calculated dose volume histogram with said prescription dose volume histogram; and delivering radiation according to said calculated dose volume histogram if said calculated dose volume histogram is within a predetermined value of said prescription dose volume histogram.

2. A method according to claim 1, wherein said opening is defined by at least one plate, the plate configured to block radiation from the radiation source.

3. A method according to claim 1, further comprising using an optimization routine to update selected openings.

4. A method according to claim 3, wherein said optimization routine is a simulated annealing routine.

5. A method according to claim 3, further comprising determining an ordering of field delivery once each field is optimized.

6. A system for delivering radiation from a source to an object, comprising:

means for delimiting predetermined radiation fields on said object;

means coupled to said delimiting means for specifying a predetermined number of said fields for delivery; and means coupled to said specifying means for constraining said delimiting means, said constraining means including means for optimizing delivery of said predetermined radiation fields, said optimizing means using settings of said delimiting means as variables when performing said optimization; and means for providing radiation according to said optimizing means, said providing means including means for providing radiation according to a calculated dose volume histogram if said calculated does volume histogram is within a predetermined value of a prescription does volume histogram.

7. A system according to claim 6, wherein said delimiting means comprises one or more plates capable of blocking radiation from the radiation source.

8. A system according to claim 7, wherein said delimiting means includes a multi-leaf collimator.

9. A system according to claim 7, wherein said specifying means includes means for specifying one or more settings of said one or more plates.

10. A system according to claim 6, wherein said optimizing means includes means for performing said optimization using simulated annealing.

11. A system according to claim 6, wherein said specifying means includes means for specifying a first dose volume histogram defining dosages to be delivered to said body.

12. A system according to claim 11, wherein said optimizing means includes means for calculating a second dose volume histogram based on said predetermined number of fields and comparing said second dose volume histogram with said first dose volume histogram.

13. A system for delivering radiation from a source to an object, comprising:

means for delimiting predetermined radiation fields on said object;

means coupled to said delimiting means for specifying a predetermined number of said fields for delivery; and means coupled to said specifying means for constraining said delimiting means, said constraining means including means for optimizing delivery of said predetermined radiation fields;

wherein said specifying means includes means for specifying a first dose volume histogram defining dosages to be delivered to said body;

wherein said optimizing means includes means for calculating a second dose volume histogram based on said predetermined number of fields and comparing said second dose volume histogram with said first dose volume histogram; and wherein said constraining means includes means for delivering said radiation according to said second dose volume histogram if said second dose volume histogram is within a predetermined value of said first dose volume histogram.

14. A system for delivering radiation from a source to an object, comprising:

a beam shielding device adapted for delimiting predetermined radiation fields on said object;

a controller adapted to specify a predetermined number of said fields for delivery; and an optimization engine adapted to determine an optimal treatment by using said beam shielding device's settings as optimization variables;

wherein said radiation is delivered according to said optimal treatment if a calculated dose volume histogram is within a predetermined value of a prescription dose volume histogram.

15. A system for delivering radiation from a radiation source to a body, said system configured to specify a prescription does volume histogram defining doses to be delivered to said body, said system characterized by:

means for specifying delivery of radiation, said specifying means responsive to said prescription dose volume histogram;

means for determining a calculated dose volume histogram responsive to said specifying means, said calculated dose volume histogram approximating said prescription dose volume histogram; and means for delivering radiation according to said calculated dose volume histogram if said calculated dose volume histogram is within a predetermined value of said prescription dose volume histogram.

16. A system for delivering radiation from a source to an object, comprising:

a beam shielding device adapted for delimiting predetermined radiation fields on said object;

a controller adapted to specify a predetermined number of said radiation fields for delivery; and an optimization engine adapted to determine an optimal treatment by using at least one of said predetermined number of radiation fields or beam shielding device settings as optimization variables;

wherein said radiation is delivered according to said optimal treatment if a calculated dose volume histogram is within a predetermined value of a prescription dose volume histogram.

17. A system for delivering radiation from a source to an object, comprising:

a beam shielding device adapted for delimiting predetermined radiation fields on said object;

a controller adapted to specify a predetermined number of said fields for delivery; and an optimization engine adapted to determine an optimal treatment by using said predetermined number of static fields as optimization variables;

wherein said radiation is delivered according to said optimal treatment if a calculated dose volume histogram is within a predetermined value of a prescription dose volume histogram.

* * * * *